United States Patent
Guo et al.

(10) Patent No.: US 8,957,220 B2
(45) Date of Patent: Feb. 17, 2015

(54) PREPARATION METHOD OF CARFENTRAZONE-ETHYL

(75) Inventors: Qunzhen Guo, Hangzhou (CN); Guoping Cai, Hangzhou (CN); Tangjun Wang, Hangzhou (CN); Jiandi Yu, Hangzhou (CN); Wei Liu, Hangzhou (CN)

(73) Assignees: Zhejiang Zhuji United Chemicals Co., Ltd, Hangzhou, Zhejiang (CN); Luzhou Oriental Agrochemicals Co., Ltd., Luzhou, Sichuan (CN)

( * ) Notice: Subject to any disclaimer, the term of this patent is extended or adjusted under 35 U.S.C. 154(b) by 0 days.

(21) Appl. No.: 14/000,170

(22) PCT Filed: Jan. 12, 2012

(86) PCT No.: PCT/CN2012/070289
§ 371 (c)(1),
(2), (4) Date: Aug. 16, 2013

(87) PCT Pub. No.: WO2012/122863
PCT Pub. Date: Sep. 20, 2012

(65) Prior Publication Data
US 2013/0345435 A1     Dec. 26, 2013

(30) Foreign Application Priority Data

Nov. 3, 2011 (CN) .......................... 2011 1 0058827

(51) Int. Cl.
C07D 249/04 (2006.01)
C07D 249/12 (2006.01)

(52) U.S. Cl.
CPC ................................... *C07D 249/12* (2013.01)
USPC ....................................................... 548/263.2

(58) Field of Classification Search
USPC ....................................................... 548/263.2
See application file for complete search history.

(56) References Cited

U.S. PATENT DOCUMENTS 5,125,958 A * 6/1992 Poss .............................. 504/273

FOREIGN PATENT DOCUMENTS

CN           102174026           *   7/2011

* cited by examiner

*Primary Examiner* — Rebecca Anderson
*Assistant Examiner* — Karen Cheng

(57) ABSTRACT

A preparation method of carfentrazone-ethyl comprises steps of: reacting 1-(5-amino-4-chloro-2-fluorophenyl)-4-difluoromethyl-3-methyl-1H-1,2,4-triazol-5-one with acrylic acid through a diazo arylation reaction to give 2-chloro-3-{2-chloro-5-[4-(difluoromethyl)-4,5-dihydro-3-methyl-5-oxo-1H-1,2,3-triazol-1-yl]-4-fluorophenyl}propionic acid; and reacting the 2-chloro-3-{2-chloro-5-[4-(difluoromethyl)-4,5-dihydro-3-methyl-5-oxo-1H-1,2,3-triazol-1-yl]-4-fluorophenyl}propionic acid with ethanol through an esterification reaction in a presence of an acidic catalyst to give carfentrazone-ethyl.

6 Claims, 2 Drawing Sheets

PREPARATION METHOD OF CARFENTRAZONE-ETHYL

CROSS REFERENCE OF RELATED APPLICATION

This is a U.S. National Stage under 35 U.S.C 371 of the International Application PCT/CN2012/070289, filed Jan. 12, 2012, which claims priority under 35 U.S.C. 119(a-d) to CN 201110058827.4, filed Mar. 11, 2011.

BACKGROUND OF THE PRESENT INVENTION

1. Field of Invention

The present invention relates to a preparation method of a compound, and more particularly to a preparation method of carfentrazone-ethyl.

2. Description of Related Arts

The carfentrazone-ethyl, namely Ethyl 2-chloro-3-[2-chloro-5-[4-(difluoromethyl)-4,5-dihydro-3-methyl-5-oxo-1H-1,2,4-triazol-1-yl]-4-fluorophenyl]propionate whose molecular formula is $C_{15}H_{14}Cl_2F_3N_3O_3$, is a triazolinone herbicide having a following structure.

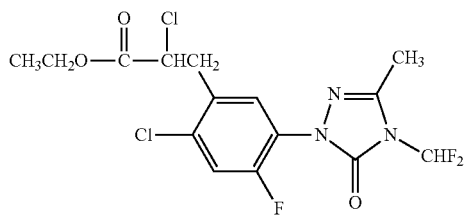

The carfentrazone-ethyl is conventionally prepared mainly by the following three methods: method one as disclosed in WO1990002120, CN1031307C and U.S. Pat. No. 5,125,958, wherein carfentrazone-ethyl is obtained via a diazotization of a 5-amino intermediate by the diazotization reagent of tert-butyl nitrite with molar quantities of copper chloride in the solvent of acetonitrile and a reaction with excess ethyl acrylate; method two as disclosed in WO1997007107, CN1068594 and U.S. Pat. No. 5,621,112, wherein carfentrazone-ethyl is obtained via a diazotization of the 5-amino intermediate hydrochloride in the aqueous solution of acetone having cuprous chloride as the catalyst and sodium nitrite as the diazotization reagent, and a simultaneous reaction with excess ethyl acrylate; and method three as disclosed in WO1999019308 and CN115301C, wherein the reaction between the 5-poition halogenated intermediate and the alkyl alkanoate in the presence of the palladium catalyst produces the alkyl propanoate having acetyl at the alpha-position which is chlorinated via sodium hypochlorite to obtain the object product, carfentrazone-ethyl.

Both method one and method two belong to Meerwein arylation and are related to diazotization reaction. As is known to those skilled in the art, diazotization reaction has many side reactions, such as thermal decomposition of diazonium salt, halogenations (Sandmeyer reaction), coupling, etc., which result in too many impurities making it difficult to obtain high quality product via the conventional purification method, since the object product is a viscous oil. Method three not only requires expensive palladium catalyst, but also suffers from the difficulty of purification.

SUMMARY OF THE PRESENT INVENTION

An objective of the present invention is to overcome the disadvantages of the prior arts and to provide a preparation method of carfentrazone-ethyl with high yield, low cost and high purity.

Accordingly, to accomplish the above objective, the present invention provides following technical solutions. A preparation method of carfentrazone-ethyl of the present invention comprises steps of:

(1) mixing 1 mol of substituted phenylamine with 16~28 mol of organic solvent, stirring to dissolve, then introducing 2.4~3.2 mol of hydrogen chloride into the mixture at a temperature between 0~5° C. and successively adding 4~12 mol of acrylic acid, 0.05 mol~0.10 mol of cuprous chloride, 0.3~0.8 mol of alkali metal chloride and a 45% (wt/wt) aqueous solution of sodium nitrite which contains 1.2~1.8 mol of sodium nitrite to react; after the reaction is completed, distilling to remove the organic solvent, adding solvent of benzene class, and washing respectively with water, acid and water; and then concentrating the organic layer under reduced pressure, cooling to crystallize, and filtrating by suction, to give 2-chloro-3-{2-chloro-5-[4-(difluoromethyl)-4,5-dihydro-3-methyl-5-oxo-1H-1,2,4-triazol-1-yl]-4-fluorophenyl}propionic acid; and (2) adding 1 mol of the 2-chloro-3-{2-chloro-5-[4-(difluoromethyl)-4,5-dihydro-3-methyl-5-oxo-1H-1,2,4-triazol-1-yl]-4-fluorophenyl}propionic acid of the step (1), 4~10 mol of ethanol and 0.03~0.2 mol of an acid catalyst into 6~12 mol of the solvent of benzene class; refluxing the reaction mixture until an esterification is completed; washing successively with water, with aqueous alkali base and then with water; and removing the solvent totally from the organic layer, to give a product carfentrazone-ethyl.

The aforementioned alkali metal chloride includes lithium chloride and potassium chloride; the solvent of benzene class includes benzene, methyl benzene and dimethyl benzene; the alkali base includes sodium carbonate, sodium bicarbonate, sodium hydroxide, potassium carbonate, potassium bicarbonate and potassium hydroxide; the acid catalyst includes concentrated sulphuric acid, trifluoroacetic acid and 4-methylbenzenesulfonic acid; and the substituted phenylamine includes 1-(5-amino-4-chloro-2-fluophenyl)-4-difluoromethyl-3-methyl-1H-1,2,4-triazol-one having a following structure.

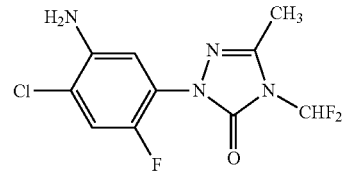 [SMILES: Cc1nn(-c2cc(N)c(Cl)cc2F)c(=O)n1C(F)F]

Compared with the prior arts, the preparation method of carfentrazone-ethyl provided by the present invention has the following advantages.

Firstly, solids of intermediate acid are able to recrystallize in a suitable solvent and a purity of more than 98% is able to be achieved.

Secondly, the esterification of the highly pure intermediate acid and ethanol in a presence of the acid catalyst results in high purity of carfentrazone-ethyl product after work-up.

Thirdly, the simple method, mild reaction conditions and the high yield make it amenable for industrial production.

These and other objectives, features, and advantages of the present invention will become apparent from the following detailed description, the accompanying drawings, and the appended claims.

DETAILED DESCRIPTION OF THE PREFERRED EMBODIMENT

Figure 1:
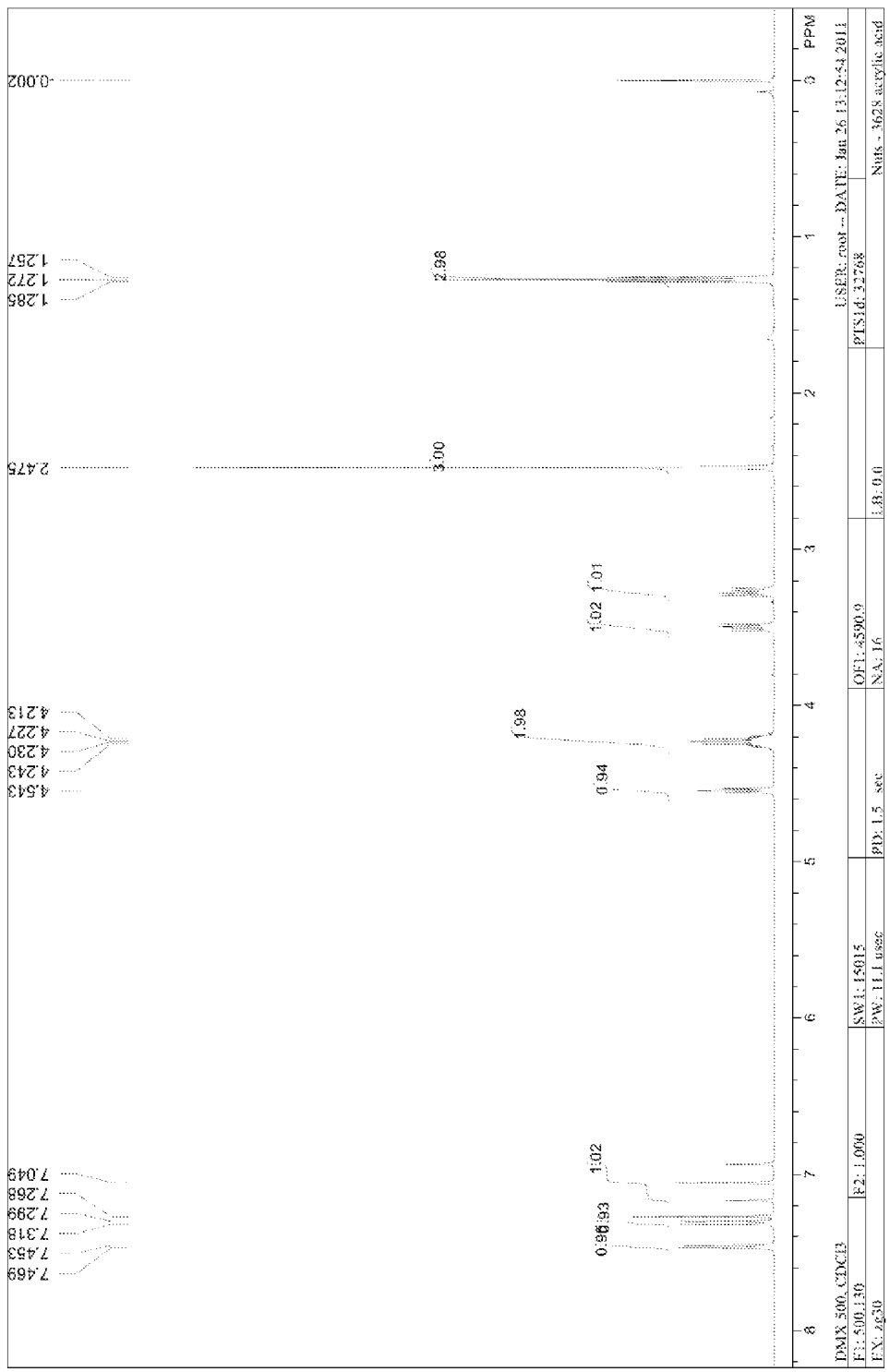
FIG. 1 is a $^1$H nuclear magnetic resonance (HNMR) spectrum of carfentrazone-ethyl according to a fifth example of the present invention.

A reaction scheme of a preparation method of carfentrazone-ethyl, provided by the present invention, is showed as follows.

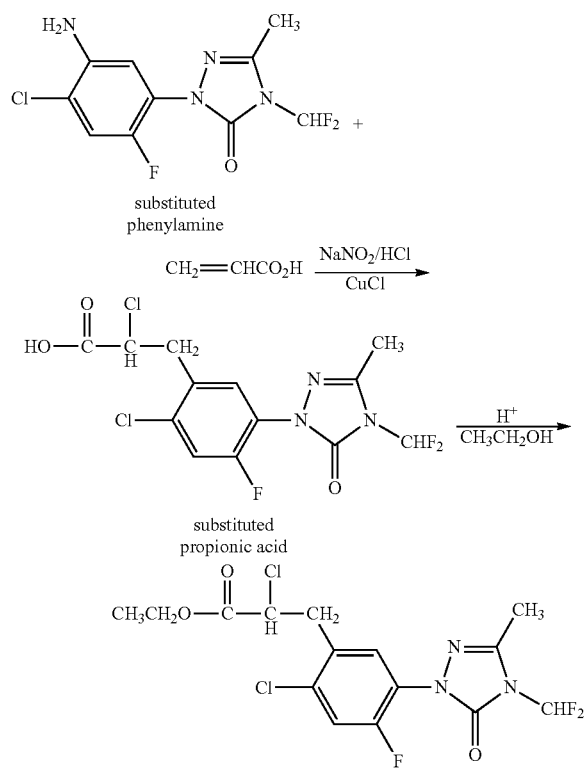

As showed in the above scheme, the preparation method of carfentrazone-ethyl comprises steps of:

(1) mixing 1 mol substituted phenylamine with 16~28 mol of organic solvent, stirring to dissolve, then introducing 2.4~3.2 mol of hydrogen chloride into the mixture at a temperature between 0~5° C. and successively adding 4~12 mol of acrylic acid, 0.05 mol~0.10 mol of cuprous chloride, 0.3~0.8 mol of alkali metal chloride and a 45% (wt/wt) aqueous solution of sodium nitrite which contains 1.2~1.8 mol of sodium nitrite to react; after the reaction is completed, distilling to remove the organic solvent, adding solvent of benzene class, and washing respectively with water, acid and water; and then concentrating the organic layer under reduced pressure, cooling to crystallize, and filtrating by suction, to give 2-chloro-3-{2-chloro-5-[4-(difluoromethyl)-4,5-dihydro-3-methyl-5-oxo-1H-1,2,4-triazol-1-yl]-4-fluorophenyl}propionic acid;

wherein the organic solvent includes acetone and acetonitrile; the alkali metal chloride includes lithium chloride and potassium chloride; the solvent of benzene class includes benzene, methyl benzene and dimethyl benzene; and the substituted phenylamine includes a 1-(5-amino-4-chloro-2-fluophenyl)-4-difluoromethyl-3-methyl-1H-1,2,4-triazol-one having a following structure; and

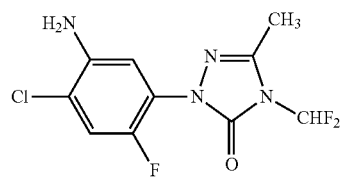 [SMILES: Cc1nn(-c2cc(N)c(Cl)cc2F)c(=O)n1C(F)F]

(2) adding 1 mol of the 2-chloro-3-{2-chloro-5-[4-(difluoromethyl)-4,5-dihydro-3-methyl-5-oxo-1H-1,2,4-triazol-1-yl]-4-fluorophenyl}propionic acid of the step (1), 4~10 mol of ethanol and 0.03~0.2 mol of an acid catalyst into 6~12 mol of the solvent of benzene class; refluxing the reaction mixture until an esterification is completed; washing successively with water, with aqueous alkali base and then with water; and removing the solvent totally from the organic layer, to give the product carfentrazone-ethyl;

wherein the solvent of benzene class includes benzene, methyl benzene and dimethyl benzene; the alkali base includes sodium carbonate, sodium bicarbonate, sodium hydroxide, potassium carbonate, potassium bicarbonate and potassium hydroxide; and the acid catalyst includes concentrated sulphuric acid, trifluoroacetic acid and 4-methylbenzenesulfonic acid.

One skilled in the art will understand that the embodiment of the present invention as shown in the schemes and drawings and described above is exemplary only and not intended to be limiting.

Example 1

Preparation of 2-chloro-3-{2-chloro-5-[4-(difluoromethyl)-4,5-dihydro-3-methyl-5-oxo-1H-1,2,4-triazol-1-yl]-4-fluorophenyl}propionic acid To a reaction flask was added a mixture of 156 g of 1-(5-amino-4-chloro-2-fluorophenyl)-4-difluoromethyl-3-methyl-1H-1,2,4-triazol-5-one and 700 g of acetone. The mixture was stirred and dissolved, and then 50 g of hydrogen chloride was introduced while maintaining a temperature between 0~5° C. 500 g of acrylic acid, 6 g of cuprous chloride and 12 g of lithium chloride were successively added. Then 115 g of a 45% aqueous solution of sodium nitrite was added dropwise below a liquid level. After the adding was completed, the mixture was stirred for additional 0.5 hour. The reaction mixture was concentrated under reduced pressure. The residue was diluted with 1000 ml of methyl benzene, washed with 300 ml of water and twice with 300 ml of a 5% diluted hydrochloride acid and then with 400 ml of water, and then concentrated under reduced pressure. After cooling, crystallized products were collected by filtration and dried, to give 174 g of 2-chloro-3-{2-chloro-5-[4-(difluoromethyl)-4,5-dihydro-3-methyl-5-oxo-1H-1,2,4-triazol-1-yl]-4-fluorophenyl}propionic acid as white solids with a purity of 98.6%.

Example 2

Preparation of 2-chloro-3-{2-chloro-5-[4-(difluoromethyl)-4,5-dihydro-3-methyl-5-oxo-1H-1,2,4-triazol-1-yl]-4-fluorophenyl}propionic acid To a reaction flask was added a mixture of 156 g of 1-(5-amino-4-chloro-2-fluorophenyl)-4-difluoromethyl-3-methyl-1H-1,2,4-triazol-5-one and 800 g of acetone. The mixture was stirred and dissolved, and then 50 g of hydrogen chloride was introduced while maintaining a temperature between 0~5° C. 500 g of acrylic acid, 6 g of cuprous chloride and 11 g of potassium chloride were successively added. Then 115 g of a 45% aqueous solution of sodium nitrite was added dropwise below a liquid level. After the adding was completed, the mixture was stirred for additional 0.5 hour. The reaction mixture was concentrated under reduced pressure. The residue was diluted with 1000 ml of methyl benzene, washed with 300 ml of water and twice with 300 ml of a 5% diluted hydrochloride acid and then with 400 ml of water, and then concentrated under reduced pressure. After cooling, crystallized products were collected by filtration and dried, to give 168 g of 2-chloro-3-{2-chloro-5-[4-(difluoromethyl)-4,5-dihydro-3-methyl-5-oxo-1H-1,2,4-triazol-1-yl]-4-fluorophenyl}propionic acid as white solids with a purity of 98.2%.

Example 3

Preparation of 2-chloro-3-{2-chloro-5-[4-(difluoromethyl)-4,5-dihydro-3-methyl-5-oxo-1H-1,2,4-triazol-1-yl]-4-fluorophenyl}propionic acid To a reaction flask was added a mixture of 156 g of 1-(5-amino-4-chloro-2-fluorophenyl)-4-difluoromethyl-3-methyl-1H-1,2,4-triazol-5-one and 900 g of acetone. The mixture was stirred and dissolved, and then 54 g of hydrogen chloride was introduced while maintaining a temperature between 0~5° C. 600 g of acrylic acid, 6 g of cuprous chloride and 8 g of lithium chloride were successively added. Then 150 g of a 45% aqueous solution of sodium nitrite was added dropwise below a liquid level. After the adding was completed, the mixture was stirred for additional 0.5 hour. The reaction mixture was concentrated under reduced pressure. The residue was diluted with 1000 ml of methyl benzene, washed with 300 ml of water and twice with 300 ml of a 5% diluted hydrochloride acid and then with 400 ml of water, and then concentrated under reduced pressure. After cooling, crystallized products were collected by filtration and dried, to give 170 g of 2-chloro-3-{2-chloro-5-[4-(difluoromethyl)-4,5-dihydro-3-methyl-5-oxo-1H-1,2,4-triazol-1-yl]-4-fluorophenyl}propionic acid as white solids with a purity of 98.5%.

Example 4

Preparation of 2-chloro-3-{2-chloro-5-[4-(difluoromethyl)-4,5-dihydro-3-methyl-5-oxo-1H-1,2,4-triazol-1-yl]-4-fluorophenyl}propionic acid To a reaction flask was added a mixture of 156 g of 1-(5-amino-4-chloro-2-fluorophenyl)-4-difluoromethyl-3-methyl-1H-1,2,4-triazol-5-one and 500 g of acetone. The mixture was stirred and dissolved, and then 45 g of hydrogen chloride was introduced while maintaining a temperature between 0~5° C. 780 g of acrylic acid, 6 g of cuprous chloride and 16 g of lithium chloride were successively added. Then 95 g of a 45% aqueous solution of sodium nitrite was added dropwise below a liquid level. After the adding was completed, the mixture was stirred for additional 0.5 hour. The reaction mixture was concentrated under reduced pressure. The residue was diluted with 1000 ml of methyl benzene, washed with 300 ml of water and twice with 300 ml of a 5% diluted hydrochloride acid and then with 400 ml of water, and then concentrated under reduced pressure. After cooling, crystallized products were collected by filtration and dried, to give 171 g of 2-chloro-3-{2-chloro-5-[4-(difluoromethyl)-4,5-dihydro-3-methyl-5-oxo-1H-1,2,4-triazol-1-yl]-4-fluorophenyl}propionic acid as white solids with a purity of 98.1%.

Example 5

Preparation of Carfentrazone-Ethyl

Figure 2:
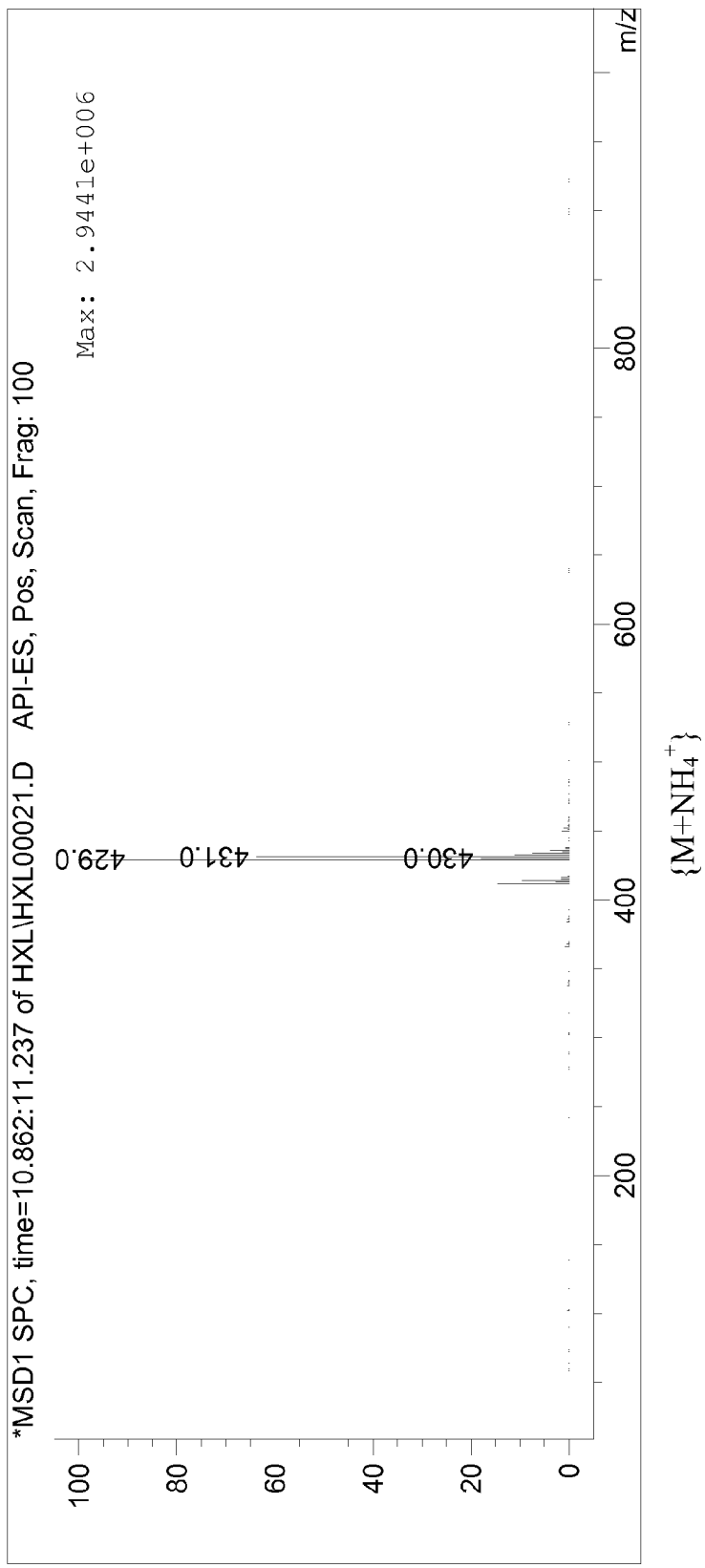
FIG. 2 is a mass spectrum of the carfentrazone-ethyl according to the fifth example of the present invention.

To a flask was added 140 g of the 2-chloro-3-{2-chloro-5-[4-(difluoromethyl)-4,5-dihydro-3-methyl-5-oxo-1H-1,2,4-triazol-1-yl]-4-fluorophenyl}propionic acid, obtained according to the Example 1, 140 g of ethanol, 1.9 g of 4-methylbenzenesulfonic acid and 400 g of dimethyl benzene. The mixture was refluxed for 15 hours to remove water. The excess ethanol was recovered by distillation. At room temperature the mixture was washed with 200 g of water, with 200 g of a 4% (wt/wt) aqueous solution of sodium hydroxide and finally with water. The solvent was completely removed under reduced pressure to give carfentrazone-ethyl as a faint yellow transparent and viscous liquid in a yield of 93% with a purity of 99%. A HNMR spectrum of the carfentrazone-ethyl is showed in FIG. 1 and a mass spectrum thereof is showed in FIG. 2.

Example 6

Preparation of Carfentrazone-Ethyl

To a flask was added 140 g of the 2-chloro-3-{2-chloro-5-[4-(difluoromethyl)-4,5-dihydro-3-methyl-5-oxo-1H-1,2,4-triazol-1-yl]-4-fluorophenyl}propionic acid, obtained according to the Example 2, 160 g of ethanol, 7 g of sulfuric acid and 700 g of methyl benzene. The mixture was refluxed for 15 hours to remove water. The excess ethanol was recovered by distillation. At room temperature the mixture was washed with 200 g of water, with 200 g of a 4% (wt/wt) aqueous solution of potassium hydroxide and finally with water. The solvent was completely removed under reduced pressure to give carfentrazone-ethyl as a faint yellow transparent and viscous liquid in a yield of 92% with a purity of 98.8%.

Example 7

Preparation of Carfentrazone-Ethyl

To a flask was added 140 g of the 2-chloro-3-{2-chloro-5-[4-(difluoromethyl)-4,5-dihydro-3-methyl-5-oxo-1H-1,2,4-triazol-1-yl]-4-fluorophenyl}propionic acid, obtained according to the Example 4, 70 g of ethanol, 1.8 g of a concentrated sulfuric acid and 500 g of methyl benzene. The mixture was refluxed for 15 hours to react. The excess ethanol was recovered by distillation. At room temperature the mixture was washed with 200 g of water, with 200 g of a 6% (wt/wt) aqueous solution of sodium carbonate and finally with water. The solvent was completely removed under reduced pressure to give carfentrazone-ethyl as a faint yellow transparent and viscous liquid in a yield of 91% with a purity of 98.2%.

Example 8

Preparation of Carfentrazone-Ethyl

To a flask was added 140 g of the 2-chloro-3-{2-chloro-5-[4-(difluoromethyl)-4,5-dihydro-3-methyl-5-oxo-1H-1,2,4-triazol-1-yl]-4-fluorophenyl}propionic acid, obtained according to the Example 3, 100 g of ethanol, 2.5 g of 4-methylbenzenesulfonic acid and 600 g of methyl benzene. The mixture was refluxed for 15 hours to remove water. The excess ethanol was recovered by distillation. At room temperature the mixture was washed with 200 g of water, with 200 g of a 4% (wt/wt) aqueous solution of sodium hydroxide and finally with water. The solvent was completely removed under reduced pressure to give carfentrazone-ethyl as a faint yellow transparent and viscous liquid in a yield of 93% with a purity of 98.6%.

What is claimed is:

1. A preparation method of carfentrazone-ethyl, comprising steps of:
    (1) mixing 1 mol of substituted phenylamine with 16-28 mol of organic solvent, stirring to dissolve, then introducing 2.4-3.2 mol of hydrogen chloride into the mixture at a temperature between 0-5° C. and successively adding 4-12 mol of acrylic acid, 0.05 mol-0.10 mol of cuprous chloride, 0.3-0.8 mol of alkali metal chloride and a 45% (wt/wt) aqueous solution of sodium nitrite which contains 1.2-1.8 mol of sodium nitrite to react; after the reaction is completed, distilling a product of the reaction to remove the organic solvent, adding a solvent of benzene class, and washing the product respectively with water, acid and water; and then concentrating an organic layer under reduced pressure, cooling to crystallize, and filtrating by suction, to give 2-chloro-3-{2-chloro-5-[4-(difluoromethyl)-4,5-dihydro-3-methyl-5-oxo-1H-1,2,4-triazol-1-yl]-4-fluorophenyl}propionic acid; and
    (2) adding 1 mol of the 2-chloro-3-{2-chloro-5-[4-(difluoromethyl)-4,5-dihydro-3-methyl-5-oxo-1H-1,2,4-triazol-1-yl]-4-fluorophenyl}propionic acid of the step (1), 4-10 mol of ethanol and 0.03-0.2 mol of an acid catalyst into 6-12 mol of the solvent of benzene class; refluxing the reaction mixture until an esterification is completed; washing successively with water, with aqueous alkali base and then with water; and removing the solvent totally from the organic layer, to give a product carfentrazone-ethyl.

2. The preparation method of the carfentrazone-ethyl according to claim 1, wherein the alkali metal chloride is lithium chloride or potassium chloride.

3. The preparation method of the carfentrazone-ethyl according to claim 1, wherein the solvent of benzene class is benzene, methyl benzene or dimethyl benzene.

4. The preparation method of the carfentrazone-ethyl according to claim 1, wherein the alkali base is one member selected from a group consisting of sodium carbonate, sodium bicarbonate, sodium hydroxide, potassium carbonate, potassium bicarbonate and potassium hydroxide.

5. The preparation method of the carfentrazone-ethyl according to claim 1, wherein the acid catalyst is concentrated sulfuric acid, trifluoroacetic acid or 4-methylbenzenesulfonic acid.

6. The preparation method of the carfentrazone-ethyl according to claim 1, wherein the substituted phenylamine is a 1-(5-amino-4-chloro-2-fluophenyl)-4-difluoromethyl-3-methyl-1H-1,2,4-triazol-one having a structure of:

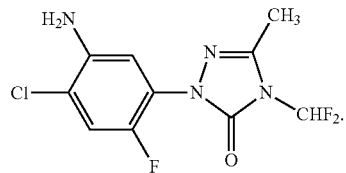 [SMILES: Cc1nn(-c2cc(N)c(Cl)cc2F)c(=O)n1C(F)F]

* * * * *